US011123529B2

(12) United States Patent
White

(10) Patent No.: US 11,123,529 B2
(45) Date of Patent: Sep. 21, 2021

(54) CHILD-RESISTANT TOPICAL DRUG APPLICATOR AND METHODS OF USE

(71) Applicant: NUTRITION & FITNESS INC., Bristol, TN (US)

(72) Inventor: Bert Cole White, Bristol, TN (US)

(73) Assignee: GREGORY PHARMACEUTICAL HOLDINGS, INC., Bristol, TN (US)

( * ) Notice: Subject to any disclaimer, the term of this patent is extended or adjusted under 35 U.S.C. 154(b) by 365 days.

(21) Appl. No.: 15/808,145

(22) Filed: Nov. 9, 2017

(65) Prior Publication Data

US 2018/0126138 A1    May 10, 2018

Related U.S. Application Data

(60) Provisional application No. 62/420,406, filed on Nov. 10, 2016.

(51) Int. Cl.
| | | |
|---|---|---|
| *A61F 13/40* | (2006.01) | |
| *B65D 50/06* | (2006.01) | |
| *B65D 41/34* | (2006.01) | |
| *B65D 50/04* | (2006.01) | |
| *A61M 19/00* | (2006.01) | |
| *B65D 47/42* | (2006.01) | |

(52) U.S. Cl.
CPC ....... *A61M 35/006* (2013.01); *B65D 41/3409* (2013.01); *B65D 50/04* (2013.01); *B65D 50/046* (2013.01); *B65D 50/061* (2013.01); *A61M 19/00* (2013.01); *A61M 2202/048* (2013.01); *A61M 2202/0468* (2013.01); *B65D 47/42* (2013.01); *B65D 2215/02* (2013.01); *B65D 2215/04* (2013.01)

(58) Field of Classification Search
CPC .......... A61M 35/006; A61M 2202/048; A61M 2202/0468; A61M 19/00; B65D 50/046; B65D 50/04; B65D 50/061; B65D 41/3409; B65D 47/42; B65D 2215/02; B65D 2215/04; B65D 50/043; B65D 50/00
See application file for complete search history.

(56) References Cited

U.S. PATENT DOCUMENTS

| | | | | |
|---|---|---|---|---|
| 3,822,805 A * | 7/1974 | Marchant | ............. | B65D 50/041 215/219 |
| 4,071,156 A * | 1/1978 | Lowe | ..................... | B65D 41/48 215/206 |
| 5,018,894 A * | 5/1991 | Goncalves | ............. | A45D 34/04 401/202 |
| 6,036,036 A * | 3/2000 | Bilani | .................. | B65D 50/046 215/216 |

(Continued)

*Primary Examiner* — Tatyana Zalukaeva
*Assistant Examiner* — Meagan Ngo
(74) *Attorney, Agent, or Firm* — Morrison & Foerster LLP

(57) ABSTRACT

Described herein is a child-resistant topical drug applicator and methods of applying a topical pharmaceutical composition to a surface. In one aspect, the child-resistant topical drug applicator comprises a container comprising a connector and a tube configured to contain a topical pharmaceutical composition, a sponge applicator fluidly coupled to the connector, and a child-resistant cap that reversibly couples to the connector and encloses the sponge applicator, the cap having a locked position and an unlocked position. Also described herein are methods of opening and using the child-resistant topical drug applicator.

30 Claims, 5 Drawing Sheets

(56) References Cited

U.S. PATENT DOCUMENTS

| | | | |
|---|---|---|---|
| 2006/0108312 A1* | 5/2006 | Robinson | B65D 50/046 215/216 |
| 2006/0285913 A1* | 12/2006 | Koptis | A45D 40/26 401/205 |
| 2013/0214004 A1* | 8/2013 | Dejonge | B65D 50/061 222/153.11 |
| 2014/0138380 A1* | 5/2014 | Fox | B65D 41/3457 220/214 |
| 2015/0050366 A1* | 2/2015 | Vlodaver | A61M 35/003 424/737 |
| 2016/0130050 A1* | 5/2016 | St. Clair | B65D 50/046 215/206 |
| 2017/0333688 A1* | 11/2017 | Parikh | A61M 35/003 |

* cited by examiner

Distal End

Proximal End

CHILD-RESISTANT TOPICAL DRUG APPLICATOR AND METHODS OF USE

CROSS-REFERENCE TO RELATED APPLICATION

This application claims priority from U.S. Provisional Patent Application No. 62/420,406, filed on Nov. 10, 2016, the contents of which are incorporated herein by reference in its entirety.

TECHNICAL FIELD

The present disclosure relates to child-resistant topical drug applicators and methods of using the same.

BACKGROUND

Topical pharmaceutical compositions are generally applied to a specific surface to be treated, for example to a limited area of the skin of a patient. Such topical pharmaceutical compositions are typically first dispensed onto a patient's or caregiver's hand or fingers and then spread on the surface to be treated by the patient or a caregiver. However, by using hands or fingers to apply the pharmaceutical composition, the drug inevitably contacts surfaces other than the surface to be treated. Gloves can be used to alleviate the undesired application of the pharmaceutical composition, but the use of gloves is cumbersome, particularly for at-home administration.

Furthermore, keeping drugs inaccessible to children, particularly young children, is a priority among drug manufacturers. In fact, the U.S. Consumer Product Safety Commission mandates child-resistant packaging for certain pharmaceutical compositions. See, e.g., United States Code of Federal Regulations 16 CFR § 1700.14 (2012). However, unlike pill bottle caps, designing an adult-friendly but child-resistant cap for a topical drug containers remains a challenge.

SUMMARY OF THE INVENTION

Provided herein, there is a child-resistant topical drug applicator comprising a container comprising a connector and a tube configured to contain a topical pharmaceutical composition; a sponge applicator fluidly coupled to the connector; and a child-resistant cap that reversibly couples to the connector and encloses the sponge applicator, the cap having a locked position and an unlocked position.

In some embodiments, the child-resistant cap comprises an inner surface having one or more protruding members; and the connector comprises an annular rim comprising one or more notches; wherein the cap is in the unlocked position when at least one protruding member is aligned with the notch, and the cap is in the locked position when the one or more protruding members are restrained by the rim. In some embodiments, the rim comprises an angled or rounded edge to allow unidirectional movement of the one or more protruding members into the locked position. In some embodiments, the connector comprises an annular grove disposed under the rim configured to receive the one or more protruding members when the cap is in the locked position. In some embodiments, the inner surface of the cap comprises two protruding members. In some embodiments, the inner surface of the cap comprises three protruding members. In some embodiments, the protruding members are approximately evenly spaced apart. In some embodiments, release of at least one of the protruding member through the notch allows for the release of the remaining protruding members.

In some embodiments, the child-resistant cap has a second locked position that limits rotational movement of the cap. In some embodiments, the connector comprises a second notch that does not fully pass through the rim, wherein the first notch and the second notch are connected by a lateral groove. In some embodiments, the second notch partially passes through the rim.

In some embodiments, the child-resistant topical drug applicator comprises a first indicator on the child-resistant cap and a second indicator on the container, wherein the first indicator and the second indicator align when the cap is in the unlocked position. In some embodiments, the first indicator aligns with one of the one or more protruding members, and the second indicator aligns with the notch in the annular rim. In some embodiments, first indicator or the second indicator is a directional indicator that indicates a direction to apply a force to remove the child-resistant cap.

In some embodiments, the child-resistant cap comprises one or more pressure points, wherein application of pressure to the pressure points configures the child-resistant cap in an unlocked position. In some embodiments, the one or more pressure points are disposed on one or more cut out tabs on the child-resistant cap.

In some embodiments, the child-resistant cap couples to the connector through a threaded interface.

In some embodiments, the child-resistant cap comprises an inner cap segment nested within an outer cap segment, and wherein the inner cap segment encloses the sponge applicator. In some embodiments, the inner cap segment couples to the connector through a threaded interface, the outer cap segment comprises one or more pressure points, and application of pressure to the pressure points positions the child-resistant cap in an unlocked position. In some embodiments, the connector comprises two or more protruding members, the child-resistant cap comprises two or more protruding members, and the protruding members of the connector block the protruding members of the child-resistant cap when the child-resistant cap is in the locked position to limit rotational movement of the cap. In some embodiments, the protruding members of the connector are angled or ratcheted.

In some embodiments, the connector is integrated with the tube. In some embodiments, the connector and the tube are separate pieces. In some embodiments, the connector is permanently attached to the tube. In some embodiments, the connector is fluidly coupled to the tube through a threaded interface. In some embodiments, the connector and the tube comprise different materials. In some embodiments, the connector comprises a first material and the connector comprises a second material, and wherein the second material is harder than the first material.

In some embodiments, the sponge applicator is permanently attached to the connector.

In some embodiments, the applicator further comprises a hole that traverses the sponge applicator and fluidly connects to the tube. In some embodiments, the cap comprises a plug that fits into the hole that traverses the sponge applicator. In some embodiments, the plug extends at least a portion of the way through the hole. In some embodiments, the plug extends into the connector. In some embodiments, the plug extends into the tube.

In some embodiments, the child-resistant topical drug applicator further comprises a hole that traverses the sponge applicator and fluidly connects to the tube. In some embodiments, the child-resistant cap comprises a plug that fits into the hole that traverses the sponge applicator.

In some embodiments, the cap comprises a grooved or textured outer surface.

In some embodiments, the connector is attached to the distal end of the tube and the proximal end of the tube is sealed.

In some embodiments, the child-resistant topical drug applicator further comprises a tamper-evident band.

In some embodiments, the tube contains the topical pharmaceutical composition. In some embodiments, the pharmaceutical composition is a topical analgesic. In some embodiments, the pharmaceutical composition comprises lidocaine. In some embodiments, the pharmaceutical composition comprises about 2% to less than 5% lidocaine by weight. In some embodiments, the pharmaceutical composition comprises about 4% lidocaine by weight. In some embodiments, the pharmaceutical composition comprises about 5% lidocaine by weight or more. In some embodiments, the pharmaceutical composition is a gel, a lotion, an ointment, a cream, or a paste. In some embodiments, the pharmaceutical composition comprises emu oil.

Further provided herein, there is a kit comprising the any of the applicators described above and instructions for use.

Further provided herein is a method of opening any one of the child-resistant topical drug applicators described above, comprising positioning in the cap in the unlocked configuration, and separating the cap from the container.

Also provided is a method of applying a topical pharmaceutical composition to a surface to be treated, comprising: separating a child-resistant cap from a container fluidly coupled to a sponge applicator, the container comprising a connector and a tube containing a topical pharmaceutical composition; and applying the pharmaceutical composition on the sponge applicator to the surface.

In some embodiments, the method further comprises dispensing the topical pharmaceutical composition disposed onto the sponge applicator.

In some embodiments of the method, the topical pharmaceutical composition is wicked up by the sponge applicator.

In some embodiments of the method, applying the pharmaceutical composition to the surface to be treated comprises rubbing or blotting the sponge applicator on the surface.

In some embodiments, the method further comprises positioning the cap to an unlocked position prior to separating the cap from the container. In some embodiments, the child-resistant cap is separated from the container by pulling or unscrewing the child-resistant cap at an angle. In some embodiments, the child-resistant cap is positioned in an unlocked position by applying pressure to one or more pressure points on the child-resistant cap.

In some embodiments of the method, the pharmaceutical composition is dispensed onto the sponge applicator by applying lateral pressure to the tube.

In some embodiments of the method, the pharmaceutical composition is a topical analgesic. In some embodiments, the pharmaceutical composition comprises lidocaine. In some embodiments, the pharmaceutical composition comprises about 2% to less than 5% lidocaine by weight. In some embodiments, the pharmaceutical composition comprises about 4% lidocaine by weight. In some embodiments, the pharmaceutical composition comprises about 5% lidocaine by weight or more. In some embodiments, the pharmaceutical composition is a gel, a lotion, an ointment, a cream, or a paste. In some embodiments, the pharmaceutical composition comprises emu oil.

Also provided herein is a child-resistant topical drug applicator for the topical application of lidocaine, comprising: a container comprising a connector and a tube containing a topical pharmaceutical composition comprising lidocaine; a sponge applicator fluidly coupled to the connector; and a child-resistant cap that reversibly couples to the connector and encloses the sponge applicator, the cap having a locked position and an unlocked position; wherein: the cap comprises an inner surface having three protruding members and a first indicator that indicates the position of one of the protruding members; the connector comprises an annular rim comprising one or more notches and a second indicator that indicates the position of the notch; the cap is in the unlocked position when one of the protruding members is aligned with the notch, and the cap is in the locked position when none of the protruding members are aligned with the notch; and the first indicator and the second indicator align when the cap is in the unlocked position. In some embodiments, the sponge applicator comprises a hole that traverses the sponge applicator and fluidly connects the tube, and wherein the child-resistant cap comprises a plug that fits into the hole that traverses the sponge applicator.

Also provided herein is a child-resistant topical drug applicator for the topical application of lidocaine, comprising: a container comprising a connector and a tube containing a topical pharmaceutical composition comprising lidocaine; a sponge applicator fluidly coupled to the connector; and a child-resistant cap that reversibly couples to the connector and encloses the sponge applicator, the cap having a locked position and an unlocked position; wherein: the child-resistant cap comprises one or more pressure points disposed on one or more cut out tabs on the child-resistant cap, wherein application of pressure to the pressure points configures the child-resistant cap in an unlocked position; the child-resistant cap comprises an inner cap segment nested within an outer cap segment; the inner cap segment couples to the connector through a threaded interface and encloses the sponge applicator; the connector comprises two or more angled or ratcheted protruding members; the child-resistant cap comprises two or more protruding members; and the protruding members of the connector block the protruding members of the child-resistant cap when the child-resistant cap is in the locked position to limit rotational movement of the cap. In some embodiments, the sponge applicator comprises a hole that traverses the sponge applicator and fluidly connects the tube, and wherein the child-resistant cap comprises a plug that fits into the hole that traverses the sponge applicator.

DETAILED DESCRIPTION

Figure 1:
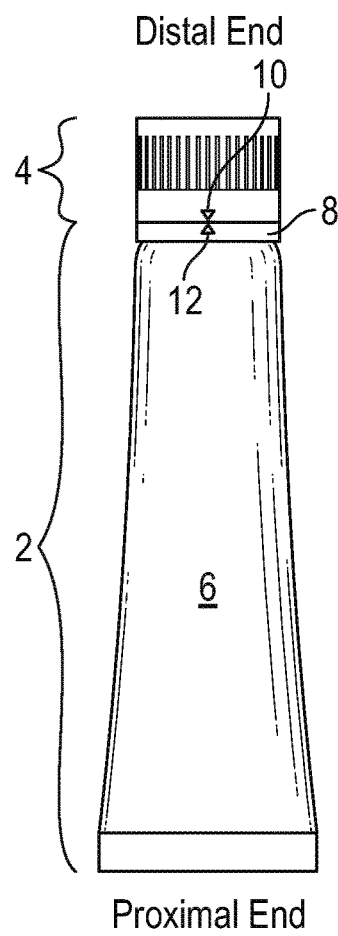
FIG. 1 illustrates one embodiment of a child-resistant topical drug applicator.

Described herein is a child-resistant topical drug applicator comprising a container comprising a connector and a tube configured to contain a topical pharmaceutical composition; a sponge applicator fluidly coupled to the connector; and a child-resistant cap that reversibly couples to the connector and encloses the sponge, the cap having a locked position and an unlocked position. Also described is a method of applying a topical pharmaceutical composition to a surface to be treated, comprising separating a child-resistant cap from a container fluidly coupled to a sponge applicator, the container comprising a connector and a tube containing a topical pharmaceutical composition; applying the pharmaceutical composition on the sponge applicator to the surface. In some embodiments, the topical pharmaceutical composition is dispensed onto the sponge.

In some embodiments, the child-resistant cap comprises an inner surface having one or more protruding members; and the connector comprises an annular rim comprising one or more notches; wherein the cap is in the unlocked position when at least one protruding member is aligned with the notch, and the cap is in the locked position when the one or more protruding members are restrained by the rim. In some embodiments, the inner surface of the cap includes two, three, or more protruding members. In some embodiments, the cap can be removed, for example, by positioning the cap in the unlocked position and pulling the cap away from the container. In some embodiments, the cap can be removed by pulling the cap away from the container at an angle when the cap is in the unlocked position.

In an exemplary embodiment, a child-resistant topical drug applicator for the topical application of lidocaine comprises a container comprising a connector and a tube containing a topical pharmaceutical composition comprising lidocaine; a sponge applicator fluidly coupled to the connector; and a child-resistant cap that reversibly couples to the connector and encloses the sponge applicator, the cap having a locked position and an unlocked position; wherein the cap comprises an inner surface having three (or more) protruding members and a first indicator that indicates the position of one of the protruding members; and the connector comprises an annular rim comprising one or more notches and a second indicator that indicates the position of the notch; wherein the cap is in the unlocked position when one of the protruding members is aligned with the notch, and the cap is in the locked position when none of the protruding members are aligned with the notch; and wherein the first indicator and the second indicator align when the cap is in the unlocked position.

In another exemplary embodiment, the child-resistant topical drug applicator for the topical application of lidocaine includes a container comprising a connector and a tube containing a topical pharmaceutical composition comprising lidocaine; a sponge applicator fluidly coupled to the connector; and a child-resistant cap that reversibly couples to the connector and encloses the sponge applicator, the cap having a locked position and an unlocked position. The child-resistant cap includes one or more pressure points disposed on one or more cut out tabs on the child-resistant cap, and application of pressure to the pressure points configures the child-resistant cap in an unlocked position. The child-resistant cap also includes inner cap segment nested within an outer cap segment, wherein the inner cap segment couples to the connector through a threaded interface and encloses the sponge applicator. The connector includes two or more angled or ratcheted protruding members, and the child-resistant cap comprises two or more protruding members. The protruding members of the connector block the protruding members of the child-resistant cap when the child-resistant cap is in the locked position to limit rotational movement of the cap.

The topical pharmaceutical composition (which can comprise, for example, a topical analgesic such as lidocaine) can be disposed within the container, such as within the tube. The cap can be separated from the container, and the pharmaceutical composition can be dispensed onto the sponge applicator. The sponge applicator containing the pharmaceutical composition can be used to apply the pharmaceutical composition on the sponge applicator a surface to be treated, for example by rubbing or blotting the sponge applicator on the surface to be treated. By dispensing the pharmaceutical composition to the sponge applicator and using the sponge applicator to apply the pharmaceutical composition to the surface to be treated, the need to first apply the pharmaceutical composition to fingers or hands is avoided.

In some embodiments sponge applicator comprises a hole that traverses the sponge applicator. In some embodiments, the pharmaceutical composition is dispensed onto the surface of sponge applicator by applying lateral pressure (i.e., by squeezing) to the tube, thereby forcing the pharmaceutical composition through the hold in the sponge applicator. In some embodiments, the cap comprises a plug that fits into the hole in the sponge applicator. In some embodiments, the plug extends at least a portion of the way (for example, a least half-way through the hole. In some embodiments, the plug extends through the whole sponge applicator. In some embodiments, the plug extends into the connector. In some embodiments, the plug extends into the tube. The plug attached to the child-resistant cap that extends into the hole of the sponge applicator can limit evaporation or drying of the pharmaceutical composition held within the container.

The child-resistant cap encloses the sponge applicator, thereby limiting access to the sponge applicator, any pharmaceutical composition that may be present on the sponge applicator, and the pharmaceutical composition disposed within the container. In certain embodiments, the child-resistant cap includes an inner cap segment and an outer cap segment, and the inner cap segment encloses the sponge applicator. Further, in some embodiments, the cap can be separated from the container without applying a downward force (i.e., by pushing down) on the cap, thereby limiting pharmaceutical composition from being squeezed from the sponge applicator (which may have absorbed pharmaceutical composition), which could otherwise cause the pharmaceutical composition to leak from the sides of the cap.

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

It is understood that aspects and variations of the invention described herein include "consisting" and/or "consisting essentially of" aspects and variations.

The terms "child-resistant" and "special packaging" are equivalent, and refer to the ease or difficulty of opening a container. A container is "child-resistant" if the container cannot be opened by at least 85% of a group of children (30% of the children aged 42-44 months, 40% of children aged 45-48 months, and 30% of children between the age 49-51 months) prior to a demonstration of how to open the container, cannot be opened by at least 80% of the group of children after a demonstration of how to open the container, and can be opened by at least 90% of adults (25% of adults aged 50-54 years, 25% of adults aged 55-59 years, and 50% of adults aged 60-70 years). The children and the adults should have no permanent or temporary illness, injury, or disability that would interfere with opening the container. Methods for determining whether a container is "child-resistant" or has "special packaging" are detailed in United States Code of Federal Regulations 16 CFR § 1700 (2012), including § 1700.20, which are hereby incorporated by reference.

The term "surface to be treated" refers to an internal or external surface on a subject, for which application of a pharmaceutical composition is desired. In some embodiments, the pharmaceutical composition is applied to a surface to be treated to alleviate one or more symptoms resulting from an injury or disease (e.g. pain or skin rash).

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

In one aspect, there is provided a child-resistant topical drug applicator comprising a container comprising a connector and a tube configured to contain a topical pharmaceutical composition; a sponge applicator fluidly coupled to the connector; and a child-resistant cap that reversibly couples to the connector and encloses the sponge applicator, the cap having a locked position and an unlocked position. In some embodiments, the topical pharmaceutical composition comprises lidocaine. In some embodiments, the applicator comprises an hole that traverses the sponge applicator and fluidly connects to the tube. In some embodiments, the cap comprises a plug that fits into the hole.

In another aspect, there is provided a child-resistant topical drug applicator comprising a container comprising a tube configured to contain a topical pharmaceutical composition and a connector comprising an annular rim comprising one or more notches; a sponge applicator fluidly coupled to the connector; and a child-resistant cap that reversibly couples to the connector and encloses the sponge applicator, the cap comprising an inner surface having one or more protruding members; wherein the cap is in an unlocked position when at least one protruding member is aligned with the notch, and the cap is in a locked position when the one or more protruding members are restrained by the rim. In some embodiments, the topical pharmaceutical composition comprises lidocaine. In some embodiments, the applicator comprises a hole that traverses the sponge applicator and fluidly connects to the tube. In some embodiments, the cap comprises a plug that fits into the hole. In some embodiments, the rim comprises an angled or rounded edge to allow unidirectional movement of the one or more protruding members into the locked position. In some embodiments, the connector comprises an annular grove disposed underneath the rim configured to receive the one or more protruding members when the cap is in the locked position.

In another aspect, there is provided a child-resistant topical drug applicator comprising a container comprising a tube configured to contain a topical pharmaceutical composition and a connector comprising an annular rim comprising one or more notches; a sponge applicator fluidly coupled to the connector; and a child-resistant cap that reversibly couples to the connector and encloses the sponge applicator, the cap comprising an inner surface having two or more (such as three or more) protruding members; wherein the cap is in an unlocked position when at least one protruding member is aligned with the notch, and the cap is in a locked position when the one or more protruding members are restrained by the rim. In some embodiments, the topical pharmaceutical composition comprises lidocaine. In some embodiments, the applicator comprises a hole that traverses the sponge applicator and fluidly connects to the tube. In some embodiments, the cap comprises a plug that fits into the hole. In some embodiments, the rim comprises an angled or rounded edge to allow unidirectional movement of the one or more protruding members into the locked position. In some embodiments, the connector comprises an annular grove disposed underneath the rim configured to receive the one or more protruding members when the cap is in the locked position. In some embodiments, release of at least one of the protruding members through the notch allows for the release of the remaining protruding members.

In another aspect, there is provided a child-resistant topical drug applicator comprising a container comprising a tube configured to contain a topical pharmaceutical composition, a connector comprising an annular rim comprising one or more notches, and a first indicator aligned with the notch; a sponge applicator fluidly coupled to the connector; and a child-resistant cap that reversibly couples to the connector and encloses the sponge applicator, the cap comprising an inner surface having two or more (such as three or more) protruding members, and an outer surface comprising a second indicator aligned with one of the protruding members; wherein the cap is in an unlocked position when at least one protruding member is aligned with the notch, and the cap is in a locked position when the one or more protruding members are restrained by the rim. In some embodiments, the topical pharmaceutical composition comprises lidocaine. In some embodiments, the applicator comprises a hole that traverses the sponge applicator and fluidly connects to the tube. In some embodiments, the cap comprises a plug that fits into the hole. In some embodiments, the rim comprises an angled or rounded edge to allow unidirectional movement of the one or more protruding members into the locked position. In some embodiments, the connector comprises an annular grove disposed underneath the rim configured to receive the one or more protruding members when the cap is in the locked position. In some embodiments, release of at least one of the protruding members through the notch allows for the release of the remaining protruding members.

In another aspect, there is provided a child-resistant topical drug applicator comprising a container comprising a connector and a tube configured to contain a topical pharmaceutical composition; a sponge applicator fluidly coupled to the connector; and a child-resistant cap that reversibly couples to the connector and encloses the sponge applicator, the cap having a locked position and an unlocked position.

In some embodiments, the child-resistant cap comprises one or more pressure points, wherein application of pressure to the pressure points configures the child-resistant cap in an unlocked position. In some embodiments, the one or more pressure points are disposed on one or more cut out tabs on the child-resistant cap. In some embodiments, the child-resistant cap couples to the connector through a threaded interface. In some embodiments, the child-resistant cap comprises an inner cap segment nested within an outer cap segment, and the inner cap segment encloses the sponge applicator. In some embodiments, the inner cap segment couples to the connector through a threaded interface, the outer cap segment comprises one or more pressure points, and application of pressure to the pressure points configures the child-resistant cap in an unlocked position. In some embodiments, the connector comprises two or more protruding members, the child-resistant cap comprises two or more protruding members, and the protruding members of the connector block the protruding members of the child-resistant cap when the child-resistant cap is in the locked position to limit rotational movement of the cap. In some embodiments, the protruding members of the connector are angled or ratcheted.

In another aspect, there is provided a method of applying a topical pharmaceutical composition to a surface to be treated, comprising separating a child-resistant cap from a container fluidly coupled to a sponge applicator, the container comprising a connector and a tube containing a topical pharmaceutical composition; and applying the pharmaceutical composition on the sponge applicator to the surface to be treated. In some embodiments, the pharmaceutical composition comprises lidocaine. In some embodiments, the pharmaceutical composition is applied to the surface to be treated by rubbing or blotting the sponge applicator on the surface to be treated.

In another aspect, there is provided a method of applying a topical pharmaceutical composition to a surface to be treated, comprising separating a child-resistant cap from a container fluidly coupled to a sponge applicator, the container comprising a connector and a tube containing a topical pharmaceutical composition; dispensing the topical pharmaceutical composition disposed onto the sponge applicator; and applying the pharmaceutical composition on the sponge applicator to the surface to be treated. In some embodiments, the pharmaceutical composition comprises lidocaine. In some embodiments, the pharmaceutical composition is applied to the surface to be treated by rubbing or blotting the sponge applicator on the surface to be treated.

In another aspect, there is provided a method of applying a topical pharmaceutical composition to a surface to be treated, comprising positioning a child-resistant cap to an unlocked position, wherein the child-resistant cap is reversibly coupled to a container comprising a connector and a tube containing a pharmaceutical composition, wherein the connector is fluidly coupled to a sponge applicator; separating a child-resistant cap from the container; dispensing the topical pharmaceutical composition disposed onto the sponge applicator; and applying the pharmaceutical composition on the sponge applicator to the surface to be treated by rubbing or blotting the sponge applicator on the surface to be treated. In some embodiments, the pharmaceutical composition comprises lidocaine.

In another aspect, there is provided a method of applying a topical pharmaceutical composition to a surface to be treated, comprising positioning a child-resistant cap to an unlocked position, wherein the child-resistant cap is reversibly coupled to a container comprising a connector and a tube containing a pharmaceutical composition, wherein the connector is fluidly coupled to a sponge applicator; separating a child-resistant cap from the container by pulling the cap away from the container (for example, by applying an upward and outward force to the child-resistant cap); dispensing the topical pharmaceutical composition disposed onto the sponge applicator; and applying the pharmaceutical composition on the sponge applicator to the surface to be treated by rubbing or blotting the sponge applicator on the surface to be treated. In some embodiments, the pharmaceutical composition comprises lidocaine.

The child resistant topical drug applicator includes a container, a sponge applicator, and a child-resistant cap. The container comprises a tube that is configured to contain a pharmaceutical composition (e.g., the topical pharmaceutical composition). The container (or tube) can be made from a flexible material, which is preferably puncture-resistant. In some embodiments, the material comprises one or more layers, which may be the same or different. The container or the one or more layers can comprise, for example, a polymer, such as polyethylene (such as low-density polyethylene), polypropylene, or ethylene vinyl alcohol. In some embodiments, the container (such as the tube) is formed using an extrusion process. In some embodiments, the tube is configured to contain between about 0.5 ounces and about 6 ounces (such as between about 0.5 ounces and about 1 ounce, about 1 ounce and about 2 ounces, about 2 ounces and about 3 ounces, about 3 ounces and about 4 ounces, about 4 ounces to about 5 ounces, about 5 ounces to about 6 ounces, about 2.5 ounces, about 2.6 ounces, about 2.7 ounces, about 2.8 ounces, or about 2.9 ounces) of the pharmaceutical composition. For reference, 1 ounce is approximately 28.3 grams. The tube can be sealed at one end of the tube (i.e. a proximal end), and is fluidly connected to a connector at the distal end of the tube. When the container includes the pharmaceutical composition disposed within the container, the pharmaceutical composition can be dispensed by applying a lateral pressure (i.e., by squeezing) to the tube, which causes the pharmaceutical composition to flow out of the tube and through a hole in the connector.

The connector is fluidly connected to the tube portion of the container and the sponge applicator, and further reversibly couples to the child-resistant cap. In some embodiments, the connector is integrated with the tube. For example, the connector and the tube can be simultaneously formed or co-extruded. In some embodiments, the connector and the tube are separate pieces, which can be attached after the tube and the connector are separately produced. In some embodiments, the connector is permanently attached to the tube, for example by applying an adhesive to the interface between the tube and the connector. In some embodiments, the tube and connector are fluidly connected through a threaded interface (which may be permanently joined, for example, by applying an adhesive). The material of the connector can be of the same material as the tube, or may be of different materials. For example, the connector can comprise polyethylene (such as low-density polyethylene or high-density polyethylene), polypropylene, polyethylene terephthalate, or ethylene vinyl alcohol. In some embodiments, the material of the connector is harder or less compressible than the material of the tube. For example, in some embodiments, a user can deform the tube (for example, by applying a lateral pressure)

The sponge applicator is fluidly coupled to the connector (for example to the distal end of the connector, wherein the proximal end of the connector is fluidly connected to the distal end of the tube). In some embodiments, the sponge applicator is permanently attached to the connector, for example through the use of an adhesive. The sponge applicator preferably comprises a material (which may be a synthetic material) that can absorb the pharmaceutical composition, but can also transfer the pharmaceutical composition to a surface to be treated upon blotting or rubbing the surface to be treated with the sponge applicator. In some embodiments, the sponge applicator is a PVA sponge (i.e. the sponge applicator comprises polyvinyl alcohol) or a polyester sponge. In some embodiments, the sponge applicator has an average pore size between about 300 micrometers and about 1000 micrometers (such as between about 300 micrometers and about 400 micrometers, between about 400 micrometers and about 500 micrometers, between about 500 micrometers and about 600 micrometers, between about 600 micrometers and about 700 micrometers, between about 700 micrometers and about 800 micrometers, between about 800 micrometers and about 900 micrometers, or between about 900 micrometers and about 1000 micrometers). In some embodiments, the sponge applicator has a circular, oval, rectangular, square, or any other suitable horizontal profile (i.e., when viewing from above the sponge applicator). In some embodiments, the sponge applicator has a conical, frusto-conical, or domed shape. The sponge applicator can include a hole that traverses the sponge applicator (and may be located in the approximate center of the horizontal profile of the sponge applicator). The hole in the sponge applicator can be fluidly connected to the contents of the tube (for example, through a hole in the connector). In some embodiments, when the pharmaceutical composition is dispensed onto the sponge, the pharmaceutical composition flows through the hole in the connector and the hole in the sponge applicator, resulting in the pharmaceutical composition being disposed on the top of the sponge.

The child-resistant cap reversibly couples to the connector and encloses the sponge applicator. The cap can be made from a polymer (such as comprise polyethylene (such as low-density polyethylene or high-density polyethylene), polypropylene, polyethylene terephthalate, ethylene vinyl alcohol) or any other suitable material. In some embodiments, the outer surface or a portion of the outer surface is textured or grooved, which can enhance grip of the cap. For example, the outer surface can comprise a plurality of longitudinal ridges along the side of the cap. In some embodiments, the cap comprises a plug that fits into the hole of the sponge applicator (if present). The plug is disposed in the interior of the cap, and can protrude from the top portion (distal end) and extend proximally towards the connector. In some embodiments, the plug extends at least half-way through the hole in the sponge applicator. In some embodiments, the plug extends into the connector (for example, into the hole of the connector). In some embodiments, the plug extends into the tube. Fitting the plug into the hole of the sponge applicator can limit leakage of the pharmaceutical composition from the container.

The child-resistant cap reversibly coupled to the connector of the container can have a locked position and an unlocked position. In the unlocked position, the cap can be separated from the connector, for example by pulling the cap away from the container when the cap is in the unlocked position or by unscrewing the cap from the connector when the cap is in the unlocked position. In some embodiments, the cap is pulled away from the container by applying an upward or an upward and outward force on the cap. In the locked position, however, the cap cannot be easily separated from the connector, thus preventing access to the pharmaceutical composition contained with the container. Optionally, the applicator includes a tamper-evident band, which can indicate that the cap had previously been separated from the container after manufacture. The tamper-evident band can be, for example, a shrink wrap that covers at least a portion (such as all) of the cap and a portion (such as all) of the container (such as a portion or all of the connector).

In some embodiments, the child-resistant cap comprises an inner surface having one or more protruding members; and the connector comprises an annular rim comprising one or more notches; wherein the cap is in the unlocked position when at least one protruding member is aligned with the notch, and the cap is in the locked position when the one or more protruding members are restrained by the rim. The protruding members are located towards or at the bottom (or proximal end) of the child-resistant cap. Optionally, the rim comprises an angled or rounded edge that allows unidirectional movement of the one or more protruding members over the rim and into the locked position. For example, the cap can be placed on the connector such that the protruding members rest on top (i.e., distal end) of the rim comprising the angled or rounded edge, and applying a downward force (i.e., pushing down) on the cap such that the protruding members slide outwardly along the angled or rounded edge before engaging the bottom portion of the rim. The bottom of the rim can include a sharp edge, which can provide for the unidirectional movement of the one or more protruding members. In some embodiments, the protruding members include an angled or rounded proximal edge. In some embodiments, the protruding members include a sharp distal edge. When the rim includes an angled or rounded edge, a user need not align the protruding member with a notch to close the container with the child-resistant cap. In some embodiments, the connector comprises an annular groove dispose underneath the rim. The annular groove is configured to receive the one or more protruding members, for example when the child-resistant cap is in the locked position. In some embodiments, the width of the annular groove is approximately the same size as the width of the protruding members, although width of the annular groove preferably is slightly larger than the size of the protruding members to permit rotation of the cap when the cap is fluidly coupled to the connector.

When the cap is in the unlocked position, a protruding member aligned with the notch can slide or pass through the notch and pass the rim. In some embodiments, the cap comprises a single protruding member on the inner surface of the cap. In some embodiments, the rim comprises a plurality of notches and the cap comprises a plurality of protruding members, wherein each protruding members aligns with a notch in the unlocked position. When the cap comprises a single protruding member (or a plurality of protruding members, wherein each protruding member aligns with a notch), alignment of the protruding member(s) with the notch(es) allow the cap to be separated from the connector by pulling the cap away from the container, as no other protruding member is restrained by the rim. In some embodiments, the cap comprises two or more (such as three or more) protruding members disposed on the inner surface of the cap, which can be evenly spaced apart. When the inner surface of the cap comprises a plurality of protruding members (i.e., two or more, or three or more), at least one protruding member can align with a notch in the unlocked position, and slide upwardly through the notch and past the rim. The remaining protruding members unaligned with a notch will not be able to slide past the rim without initially passing the first protruding member through the notch and past the rim. However, once the first protruding member passes the rim, the remaining protruding members can disengage from the rim, for example by passing around the rim. Thus, in some embodiments, the cap can be separated from the connector by pulling the cap away from the container at an angle, which would allow the first protruding member to pass the rim by sliding past the notch, thereby allowing the remaining protruding members to release from the rim.

In some embodiments, the child-resistant cap, once coupled to the connector, can be rotated. Rotation of the cap can position the cap into the unlocked position or the locked position (for example, by aligning or un-aligning one or more of the protruding members from the notch in the annular ring). In some embodiments, an indicator on the child-resistant cap can indicate the position of a protruding member. The indicator can be located, for example, on the outer surface of the cap opposite from the protruding member, which is located on the inner surface. A second indicator (which can be located on the outer surface of the container, such as the outer surface of the connector or the outer surface of the tube) can indicate the position of a notch in the annular ring, for example by being placed below the notch. The second indicator should be visible when the cap is fluidly connected to the connector. When the first indicator and the second indicator are aligned (for example, by rotating the child-resistant cap), the protruding member is aligned with the notch and the cap is in the unlocked position. The indicators can be, for example, printed onto the cap or the container, or can be raised from the surface of the cap or the container. In some embodiments, the indicators are arrows or triangles, wherein the point of the arrow or the triangle indicates the position of the notch or the protruding member.

In some embodiments, the inner surface of the child-resistant cap comprises a plurality of protruding members restrained by a rim comprising a notch, a first indicator located on the cap that aligns with one of the protruding members, and a second indicator located on the container that aligns with the notch. Aligning the indicators positions the child-resistant cap in the unlocked position. It would be most natural for a user to align the indicators with the indicators facing the user. One particular advantage of this configuration is that the notch and the protruding member are also facing the user (although covered by the cap), which allows for natural biomechanical movement to apply an upward and angled (i.e., away from the body) force to the cap which, as described above, allows the first protruding member to slide through the notch and past the rim, thereby releasing the remaining protruding members. Thus, the indicator on the cap or the container can also be a directional indicator that indicates the direction to pull the cap to remove the cap from the container.

In some embodiments, the child-resistant cap comprises a second locked position that limits rotational movement of the cap. For example, in some embodiments, the child-resistant cap comprises an inner surface having one or more protruding members; and the connector comprises an annular rim comprising a first notch, and a second notch that does not fully pass through the rim, the second notch being connected to the first notch by a lateral groove; wherein the cap is in the unlocked position when at least one protruding member is aligned with the notch, the cap is in a first locked position when the one or more protruding members are restrained by the rim; and the cap is in the second locked position when the protruding member fits into the second notch. Second notch may partially pass through the rim (i.e., it is disposed in a distal direction relative to the lateral groove), or it may be disposed in a proximal direction relative to the lateral groove. The protruding member can slide along the lateral groove and enter the second notch (for example, by moving in the direction of second notch, either proximally or distally). Once the protruding member is in the second notch, rotation of the child-resistant cap is limited and is thus in the second locked position. To open the child-resistant cap, the cap can be manipulated (for example by applying an upward or downward force on the cap, depending on the direction of the second notch) to dislodge the protruding from the second notch to the lateral groove. Once the protruding member is in the lateral grove, the cap can be rotated to position the cap in the unlocked configuration by aligning the protruding member with the first notch. A partial rotation of the cap such that the protruding member is unaligned with either the first notch or the second notch allows the protruding member to be restrained by the rim, which positions the cap in the first locked position.

In some embodiments, the child-resistant cap includes a default locked position when attached to the connector, and a configurable unlocked position. For example, in certain embodiments, the child-resistant cap can be configured into the unlocked position by applying pressure to the outer surface of the cap. Pressure applied to pressure point on the outer surface of the cap can distort the shape of the cap, which positions the cap in an unlocked position. For example, in some embodiments, the child-safety cap includes one or more (such as two) protruding member on the proximal edge or within the inside of the cap (such on the inner surface of the cap), and the connector can include one or more (such as two) hooks or protruding members. In the locked position, the protruding member(s) on the child-safety cap engage the protruding members on the connector to prevent the child-safety cap from separating from the connector. The child-safety cap can include one or more pressure points (such as two, which are on opposite sides of the child-safety cap), which, when pressure is applied, can distort the cap to move the protruding members on the cap, thereby configuring the cap in the unlocked position. Once the child-resistant cap is in the unlocked position it can be separated from the connector.

In some embodiments, the child-safety cap attaches to the connector through a threaded interface. That is, the outer surface of the connector includes a threaded interface that engages a threaded surface on the inner surface of the child-safety cap. When the child-safety cap is in the locked position, the child-safety cap cannot be unscrewed and disconnected from the connector. However, once the child-safety cap is configured in the unlocked configuration (for example, by applying pressure to the pressure points on the cap), the child-safety cap can be unscrewed and disconnected from the connector. In certain embodiments, the protruding members on the connector are angled or ratcheted. For example, when the child-safety cap is attached to the connector by screwing the cap onto the connector, the protruding member on the cap can flex around the protruding member on the connector by way of the angled or ratcheted shape before snapping into the locked position. The protruding member(s) on the connector block the protruding member(s) on the cap when attempting to unscrew the cap. Applying pressure to the pressure points of the cap can distort the shape of the cap to flex the protruding members of the cap such that they can move past the protruding member(s) of the connector, either on the inside or outside of the protruding members of the connector. In some embodiments, the pressure points are orthogonal to the protruding member(s) on the cap, and applying pressure to the pressure points causes the protruding member(s) on the cap to flex outwardly. In some embodiments, the pressure points are proximal to the protruding member(s) on the cap, and applying pressure to the pressure points causes the protruding member(s) on the cap to flex inwardly.

In certain embodiments, the child-safety cap includes an inner cap segment and an outer cap segment, with the inner cap segment nested within the outer cap segment. The inner surface of the inner cap can include a threaded interface, which can engage the threaded outer surface of the connector. The outer cap can include one or more (such as two) pressure points, which are used to configure the child-safety cap to the unlocked position. The cuter cap can further include or be connected to the protruding member(s), which can engage the protruding member(s) on the connector. In some embodiment, the protruding member(s) of the child-safety cap are disposed between the inner cap segment and the outer cap segment, and can be connected (for example, by a bridge) to the pressure points on the outer cap. In some embodiments, the pressure points on the outer cap are on cut out tabs. The cut out tab allow increased flexing of the protruding member of the cap, which could otherwise be limited in smaller child-safety caps.

The pharmaceutical composition disposed within the container can be applied to a surface to be treated, such as skin of a subject. For example, pharmaceutical composition on the sponge applicator can be applied to the surface to be treated by blotting or rubbing the sponge applicator on the surface to be treated. In some embodiments, the pharmaceutical composition is dispensed onto the sponge applicator by applying lateral pressure (e.g., by squeezing) to the tube of the container after the child-resistant cap has been separated from the container. The lateral pressure forces the pharmaceutical composition in the tube to pass to the sponge applicator. In some embodiments, the pharmaceutical composition passes through the connector (for example, through a hole in the connector) and to the sponge applicator. In some embodiments, the sponge applicator comprises a hole, and the pharmaceutical composition can pass through the hole in the sponge applicator and to the upper surface of the sponge applicator.

In some embodiments, the pharmaceutical composition is wicked up by the sponge applicator. For example, the sponge applicator can be fluidly connected to the pharmaceutical composition in the tube. The pharmaceutical composition can pass through the sponge applicator (which may or may not include a hole), for example by applying a lateral pressure (i.e., squeezing) the tube to force the pharmaceutical composition into the sponge applicator or by a capillary force that draws the pharmaceutical composition into the sponge applicator. The pharmaceutical composition can pass through pores in the sponge applicator to the outer surface of the sponge applicator.

In some embodiments, the child-resistant cap is separated from the container by pulling the cap away from the container. For example, in some embodiments, the inner surface of the cap comprises one or more protruding members that each aligns with a notch in the rim such that no protruding member is restrained by the rim in the unlocked position. Pulling the cap away from the container allows the protruding members to move through the notches and past the rim. In some embodiments, the child-resistant cap is separated from the container pulling the cap away from the container at an angle (i.e., away from the user opening separating the cap) force on the container. For example, in some embodiments, the inner surface of the cap comprises a plurality of prongs (such as two or more, or three or more) and at least one protruding member aligns with a notch in the unlocked position. Pulling the cap allows the first protruding member to pass through the notch and past the rim, and the angled direction allows the remaining protruding members to disengage from the rim.

In some embodiments, separating the child-resistant cap from the container comprises positioning the cap to an unlocked position prior to separating the cap from the container. For example, the cap can be rotated to align a protruding member with a notch. By rotating the cap, the protruding members slide along the bottom of the rim, for example in the annular groove positioned below the rim. In some embodiments alignment of the protruding member with the notch is aided by an indicator. For example, a user can rotate the cap such that a first indicator on the outer surface of the cap with a second indicator on the container, which indicates that the protruding member aligns with the notch. In some embodiments, the user positions the applicator such that the aligned indicators face the user. By positioning applicator such that the aligned indicators face the user, the direction of the outward for applied to the child-resistant cap is more apparent to the user.

In some embodiments, separating the child-resistant cap from the container includes pushing down on the cap or pulling on the cap prior to rotating the cap. For example, in some embodiments, the child-resistant cap comprises a second locked position that limits rotational movement of the cap. The protruding member of the cap can be positioned in the second notch that does not fully pass through the rim, which limits the rotational movement. By pushing down on or pulling up on (depending on the direction of the second notch) the cap, the protruding member can be positioned in a lateral groove, which allows the cap to be rotated. The cap can be rotated to align the protruding member with the first notch that in the rim, and the cap can be separated from the container by pulling the cap away from the container.

In some embodiments, separating the child-resistant cap from the container includes applying pressure to one or more pressure points on the outer surface of the cap, thereby distorting the shape of the cap, and unscrewing or pulling the cap to separate the cap from the container. Applying pressure to the pressure points flexes protruding members attached to the cap such that the protruding members can pass inside or outside of protruding members attached to the connector when the child-resistant cap is separated from the container.

In some embodiments, the topical pharmaceutical composition comprises a topical analgesic. For example, in some embodiments, the pharmaceutical composition comprises lidocaine. In some embodiments, the pharmaceutical composition comprises about 10% lidocaine by weight or less (such as about 9% or less, about 8% or less, about 7% or less, about 6% or less, about 5% or less, about 4% or less, about 3% or less, about 2% or less, or about 1% or less). In some embodiments, the pharmaceutical composition comprises about 0.5% lidocaine by weight or more (such as about 1% or more, 2% or more, about 3% or more, about 4% or more, about 5% or more, about 6% or more, about 7% or more, about 8% or more, or about 9% or more). In some embodiments, the pharmaceutical composition comprises about 0.5% to about 10% lidocaine by weight (such as about 0.5% to about 1%, about 1% to about 2%, about 2% to about 3%, about 3% to about 4%, about 4% to about 5%, about 5% to about 6%, about 6% to about 7%, about 7% to about 8%, about 8% to about 9%, or about 9% to about 10%). In some embodiments, the pharmaceutical composition comprises less than 5% lidocaine by weight. In some embodiments, the pharmaceutical composition comprises about 5% lidocaine by weight or more. In some embodiments, the pharmaceutical composition comprises about 0.5%, about 1%, 2% or more, about 3%, about 4%, about 5%, about 6%, about 7%, about 8%, about 9%, or about 10% lidocaine by weight.

In some embodiments, the pharmaceutical composition comprises menthol, methylsalicylate, camphor, capsaicin, diofenac, tetracine, benzocaine, prilocaine, any other anesthetic, a salicylate (such as aspirin), ibuprofen, or any other nonsteroidal anti-inflammatory drug (NSAID).

In some embodiments, the topical pharmaceutical composition comprises an anti-acne agent, an anesthetic, an anti-infective agent, an antibiotic agent, an antifungal agent, an antineoplastic, an antipsoriatic, an antiviral, an anstrignent, or an antiviral agent.

In some embodiments, the pharmaceutical composition comprises or further comprises emu oil.

In some embodiments, the pharmaceutical composition is a gel, a lotion, an ointment, a cream, or a paste. The pharmaceutical composition can comprise one or more pharmaceutically acceptable carriers. The choice of a suitable carrier will depend on the exact nature of the particular formulation desired, e.g., whether the pharmaceutical composition is a gel, a lotion, an ointment, a cream, or a paste. Suitable pharmaceutically acceptable carriers will be apparent to those skilled in the art. See also *Remington: The Science and Practice of Pharmacy*, 20th Edition, Lippincott, Williams & Wilkins (2000). Typical pharmaceutically acceptable carriers include, but are not limited to, mannitol, urea, dextrans, allantoin, lactose, potato and maize starches, magnesium stearate, talc, vegetable oils, polyalkylene glycols, ethyl cellulose, poly(vinylpyrrolidone), calcium carbonate, chitosan, ethyl oleate, isopropyl myristate, benzyl benzoate, sodium carbonate, gelatin, potassium carbonate, silicic acid, aloe barbadensis leaf juice (aloe vera), and other conventionally employed acceptable carriers. Other carriers include, but are not limited to, phosphatidylcholine, phosphatidylserine, and sphingomyelins.

The carrier can also be selected from various oils, including those of petroleum, animal, vegetable, or synthetic origin (e.g. peanut oil, soybean oil, mineral oil, sesame oil, caprylic/capric triglycerides and the like). Suitable pharmaceutical carriers include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical processes, such as sterilization, and can contain conventional pharmaceutical additives, such as preservatives, stabilizing agents, reducing agents, anti-oxidants, chelating agents, wetting agents, emulsifying agents, dispersing agents, jelling agents, salts for adjusting osmotic pressure, buffers, and the like. The lists of carriers and additives discussed herein are by no means complete and a worker skilled in the art can choose carriers and excipients from the GRAS (generally regarded as safe) list of chemicals allowed in pharmaceutical preparations and those that are currently allowed in topical and parenteral formulations. (See also Wang et al., (1980) *J. Parent. Drug Assn.*, 34:452-462; Wang et al., (1988) *J. Parent. Sci. and Tech.*, 42:S4-S26.)

Additional carriers that can be included in the pharmaceutical composition are a bioadhesive to retain the agent at the site of application. A bioadhesive can refer to hydrophilic polymers, natural or synthetic, which, by the hydrophilic designation, can be either water soluble or swellable and which are compatible with the pharmaceutical composition. Such adhesives can include, but are not limited to, hydroxypropyl cellulose, hydroxypropyl methylcellulose, hydroxyethyl cellulose, ethyl cellulose, carboxymethyl cellulose, dextran, gaur gum, polyvinyl pyrrolidone, pectins, starches, gelatin, casein, acrylic acid polymers, polymers of acrylic acid esters, acrylic acid copolymers, acrylates/acrylamide copolymer, vinyl polymers, vinyl copolymers, polymers of vinyl alcohols, alkoxy polymers, polyethylene oxide polymers, polyethers, and combinations thereof.

The child-resistant applicator and be included as part of a kit, which can further include instructions for use. In some embodiments, the kit comprises the applicator contained within a box or other suitable outer packaging. In some embodiments, the box or other suitable packaging comprises a tamper evident seal, such as a shrink wrap that encloses the box or a tamper-evident tape that holds an opening of the box in a closed position. The instructions can be printed on the applicator itself (such as on the container), a sheet included with the applicator, or on the box or other suitable outer packaging. The instructions can include, for examples, instructions for how to open the applicator (for example, how to position the child-resistant cap in the locked or unlocked position) or how to apply the pharmaceutical composition. In some embodiments, instructions (such as how to open the applicator or how to apply the pharmaceutical composition) for use are included on the child-resistant cap. Instructions on the child-resistant cap can be, for example, printed or raised from the surface of the cap. In one exemplary embodiment, the instructions on the cap include arrows indicating the direction to rotate the cap to position the cap in a locked position or an unlocked position. In some embodiments, the instructions include warnings, indications, or ingredients of the pharmaceutical compositions (such as active ingredients or inactive ingredients).

FIG. 1 illustrates one embodiment of a child-resistant topical drug applicator. Proximal (downward) and distal (upward) directions are indicated. The applicator includes a container 2 and a child-resistant cap 4. The container 2 includes a tube 6 configured to contain a pharmaceutical composition, and a connector 8. The proximal end of the tube 6 is sealed, and the connector 8 is fluidly connected to the tube 6 at the distal end of the tube 6. In the embodiment illustrated in FIG. 1, the connector 8 is a separate piece from the tube 6, and can be permanently attached to the tube 6, for example by use of an adhesive. The sponge applicator is fluidly coupled to the connector 8, although the sponge applicator is enclosed by the child-resistant cap 4 and therefore not visible in FIG. 1. The child-resistant cap 4 reversibly couples to the connector 8, and can have a locked position and an unlocked position. The child-resistant cap 4 includes a first indicator 10, and the connector 8 includes a second indicator 12. In FIG. 1, the first indicator 10 and the second indicator 12 are aligned, indicating that the child-resistant cap is in the unlocked position. The child-resistant cap 4 includes a textured surface on the outer sides of the child-resistant cap 4, which can provide for enhanced grip when rotating or pulling the cap.

Figure 2A:
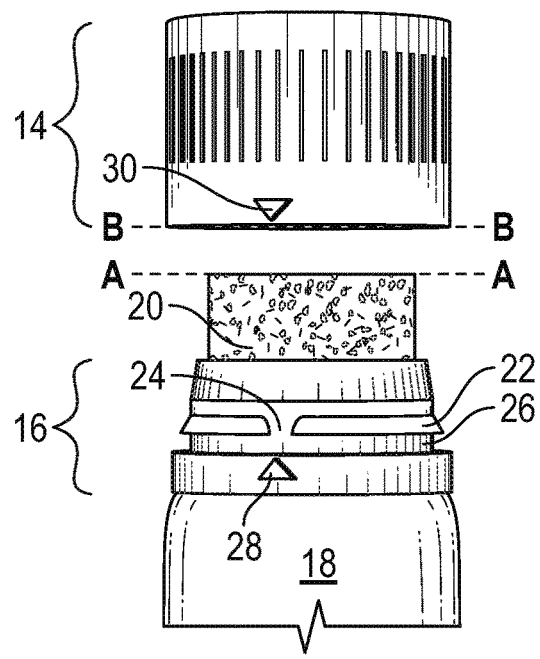
FIG. 2A illustrates the distal end of the child-resistant topical drug applicator with the child-resistant cap separated from the container.

FIG. 2A illustrates the distal end of the child-resistant topical drug applicator with the child-resistant cap 14 separated from the container. The container includes a connector 16 fluidly coupled to the tube 18. The applicator further includes a sponge applicator 20 fluidly coupled to the connector 16. The connector 16 includes an annular rim 22, which includes a notch 24. On the inner surface of the child-resistant cap 14, there a protruding member (not shown in FIG. 2A), which can align with the notch 24 in the unlocked position, and which is restrained by the rim 22 in the locked position. The rim 22 has an angled edge on the distal side of the rim 22, which allows for unidirectional movement of the protruding members into the locked position when the child-resistant cap 14 is coupled to the connector 16. Underneath the annular rim 22 is an annular groove 26, which is configured to receive the protruding members. The connector 16 further includes an indicator 28 that aligns with the notch 24. The child-resistant cap 14 also includes an indicator 30, which aligns with a protruding member on the inner surface of the child-resistant cap 14.

Figure 2B:
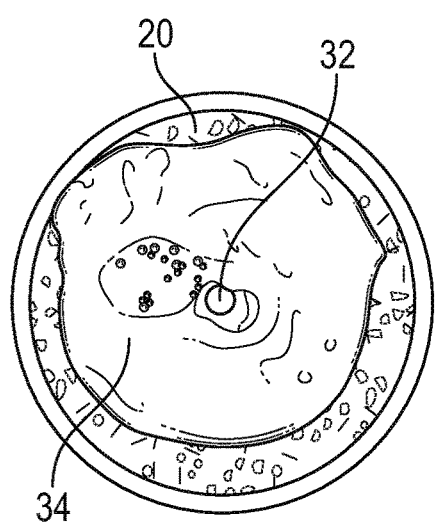
FIG. 2B is a cross-sectional image of the sponge applicator viewed from above (looking towards the proximal end) at a plane marked "A" in FIG. 2A.

FIG. 2B is a cross-sectional image of the sponge applicator 20 viewed from above (looking towards the proximal end) at a plane marked "A" in FIG. 2A. The sponge applicator 20 includes a hole 32 through the approximate center of the sponge applicator 20. Pharmaceutical composition 34 disposed within the container (for example in the tube 18) can be dispensed onto the sponge applicator 20. For example, the pharmaceutical composition 34 can flow from the tube 18 through a hole in the connector 16, and then through the hole 32 in the sponge applicator 20.

Figure 2C:
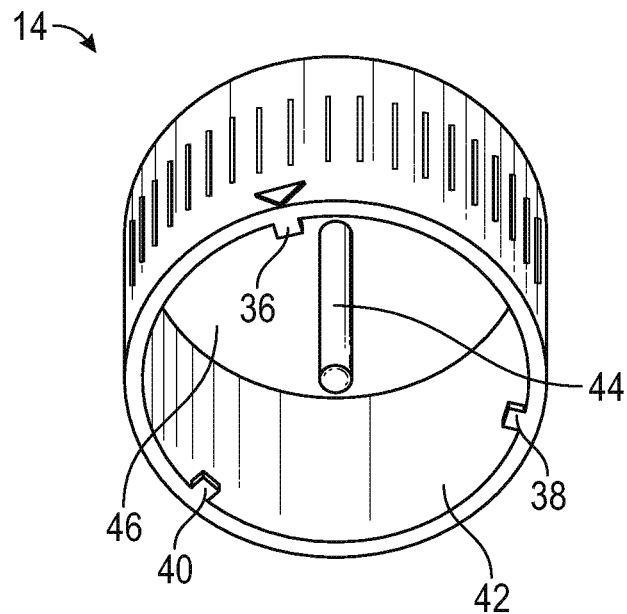
FIG. 2C is a cross sectional image of the child-resistant cap viewed from below (looking towards the distal end) at a plane marked "B" in FIG. 2A.

FIG. 2C is a cross sectional image of the child-resistant cap 14 viewed from below (looking towards the distal end) at a plane marked "B" in FIG. 2A. The child-resistant cap 14 includes a first protruding member 36, a second protruding member 38, and a third protruding member 40 located on the proximal end of the inner surface sidewall 42 of the child-resistant cap. The child-resistant cap 14 also includes a plug 44 attached to the inner surface top 46 of the child-resistant cap. The plug 44 extends distally, and can reach to or through the hole 32 in the sponge applicator 20.

Figure 3:
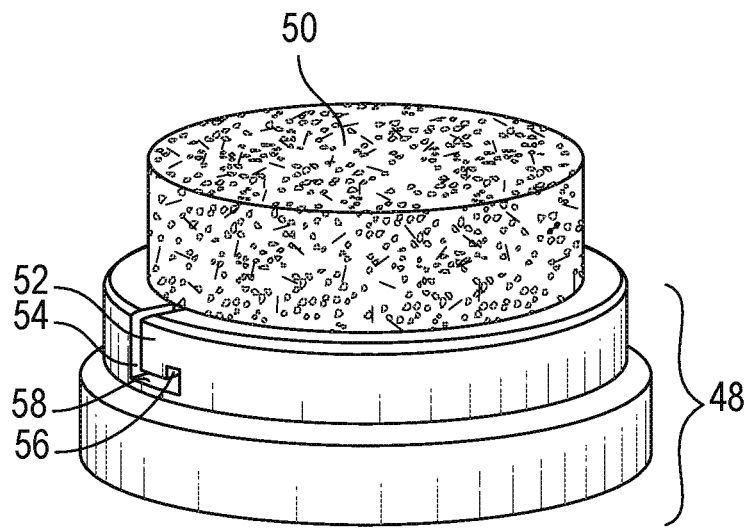
FIG. 3 illustrates an exemplary embodiments of a connector coupled to a sponge applicator that can provide for the second locked position.

In some embodiments, the child-resistant drug applicator comprises a second locked position. FIG. 3 illustrates an exemplary embodiments of a connector fluidly coupled to a sponge applicator that can provide for the second locked position. The connector 48 can be fluidly connected to a tube (not shown) at the proximal end of the connector 48. A sponge applicator 50 is fluidly connected to the distal end of the connector 48. The connector 48 includes a rim 52, which comprises a first notch 54. The connector 48 further comprises a second notch 56 that does not fully pass through the rim 52. The second notch 56 is connected to the first notch 54 by a lateral groove 58. A protruding member on an inner surface of a child-resistant cap can pass through the first notch 54 in the rim 52 to separate or reversibly couple the child-resistant cap to the connector 48. When the child-resistant cap is coupled to the connector 48 in the unlocked position, the protruding members are aligned with the first notch 54. The child-resistant cap can be rotated to slide the protruding member along the lateral groove 58 until the protruding member aligns with the second notch 56. Once aligned with the second notch 56, the child-resistant cap can be moved upwardly (in the embodiment illustrated in FIG. 3), thereby positioning the child-resistant cap in the second locked position. Once in the second locked position, rotation of the child-resistant cap is limited. To uncouple the child-resistant cap from the connector 48 once in the second unlocked position, the child-resistant cap can be moved downwardly, allowing the protruding member to align with the lateral groove 58. Once the protruding member is aligned with the lateral groove, the child-resistant cap can be rotated to align the protruding member with the first notch 54, thereby positioning the cap in the unlocked position. As the child-resistant cap is rotated from the alignment of the protruding member with the second notch 56 to the first notch 54, the protruding member is restrained by the rim 52, and is thus considered to be in the first locked position.

Figure 4A:
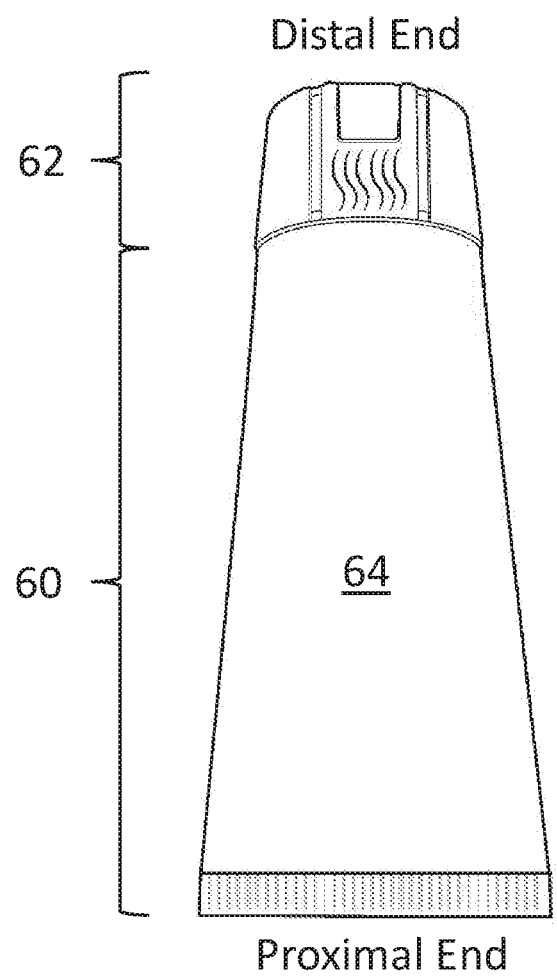
FIG. 4A illustrates another embodiment of a child-resistant topical drug applicator.
Figure 4B:
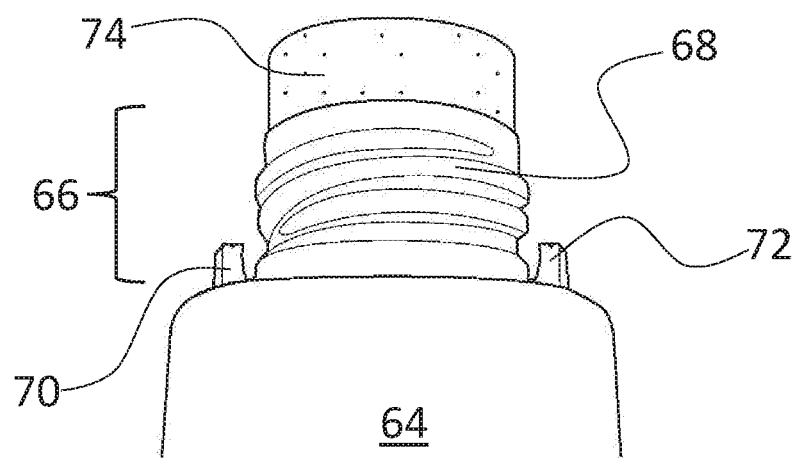
FIG. 4B illustrates the distal end of the child-resistant topical drug applicator illustrated in FIG. 4A without the child-resistant cap.
Figure 4C:
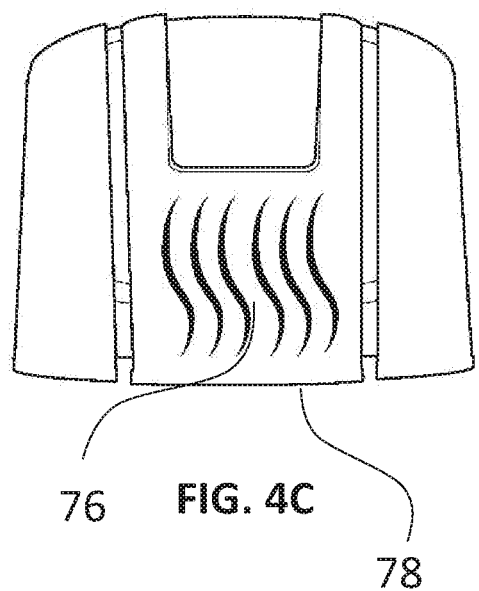
FIG. 4C illustrates the child-resistant cap of the child-resistant topical drug applicator illustrated in FIG. 4A.

FIG. 4A illustrates another embodiment of a child-resistant topical drug applicator, with proximal (downward) and distal (upward) directions indicated. The applicator includes a container 60 and a child-resistant cap 62. The container 60 includes a tube 64 configured to contain a topical pharmaceutical composition and a connector 66. The proximal end of the tube 64 is sealed. In FIG. 4A, the connector is fully enclosed by the child-resistant cap 62, but an uncapped distal portion of the container 60 is shown in FIG. 4B. The connector 66 is integrally connected at the distal end of the tube 64. The distal end of the connector 66 includes a threaded surface 68, which can engage the child-resistant cap 62. The proximal end of the connector 66 includes two protruding members 70 and 72. The sponge applicator 74 is fluidly coupled to the connector 66 at the distal end. FIG. 4C shows a zoomed in view of the child-resistant cap 62, which engages the connector 66 to enclose the sponge applicator 74. The outer surface of the child-resistant cap 62 includes two pressure points 76, one on opposite sides of the cap 62. Optionally, the pressure points 76 are marked with an indicator, indentation, or ridges, which can be used to indicate the pressure points or can enhance grip at that location. In some embodiments, the pressure point 76 is on a cut out tab 78, which is separated from the rest of the cap by cut out segments on either side of the tab.

Figure 4D:
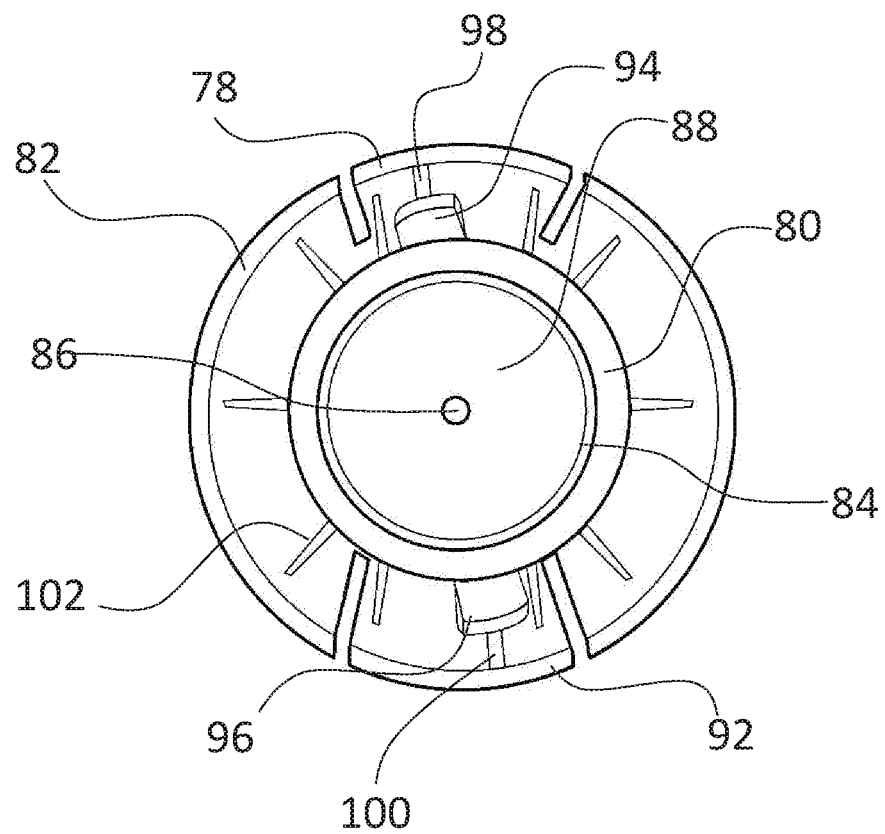
FIG. 4D illustrates another view of the child-resistant cap of the child-resistant topical drug applicator illustrated in FIG. 4A, as viewed from the proximal end.
Figure 4E:
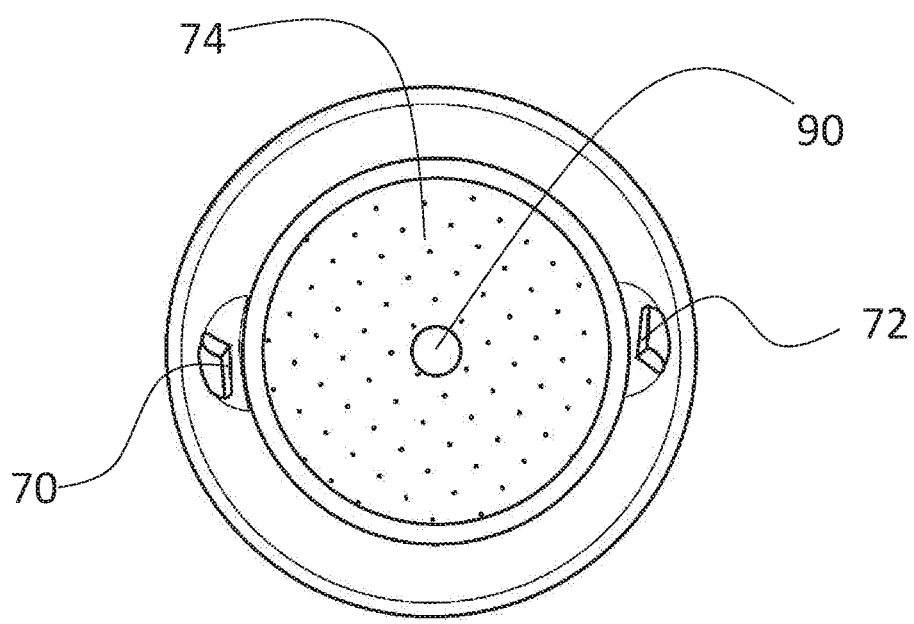
FIG. 4E illustrates another view of the distal end of the child-resistant topical drug applicator illustrated in FIG. 4A without the child-resistant cap, as viewed from the distal end.

A view of the inside of the child-resistant cap 62, as viewed from the proximal end, is shown in FIG. 4D. The child-resistant cap includes an inner cap segment 80 nested within an outer cap segment 82. The inner cap segment 80 includes an inner threaded surface 84, which engages the outer threaded surface 68 of the connector 66 when the child-resistant cap 62 is attached to the connector 66 to enclose the sponge applicator 74. The inner cap 80 includes a plug 86 attached to the inner surface top 88 of the inner cap segment 80. The plug 86 extends distally, and can reach to or through a hole 90 in the sponge applicator 74. The hole 90 in the sponge applicator 74 is shown in FIG. 4E. The plug 86 extending into or through the hole 90 in the sponge applicator 74 helps minimize evaporation from the contents within the container (e.g., the topical pharmaceutical composition). In the embodiment illustrated in FIG. 4D, the outer cap segment 82 includes the cut out tabs 78 and 92, the outer surface of which include the pressure points. The tabs 78 and 92 are bridged to protruding members 94 and 96. The outer surface of protruding member 94 is bridged to the inner surface of tab 78 by bridge 98, and the outer surface of protruding member 96 is bridged to the inner surface of tab 92 by bridge 100. The inner surface of protruding members 94 and 96 are unattached. Optionally, the top surface of the child-resistant cap 62 includes a plurality of stability bridges 102, which help maintain the portions of the cap that are not intended to flex.

When pressure is applied to the pressure points on the outer surface of tabs 78 and 92, the protruding members 94 and 96 are flexed inwardly. When the child-resistant cap 62 is placed on the container 60, the plug 86 extends into the hole 90 in the center of the sponge applicator 74. The threaded inner surface 84 of the inner cap segment 80 can engage the threaded outer surface 68 of the connector 66, and the child-resistant cap 62 can be screwed clockwise (when looking from the distal end to the proximal end). As shown in FIG. 4E, the protruding members 70 and 72 of the connector 66 are ratcheted. When the protruding members 94 and 96 of the child-resistant cap 62 encounter the protruding members 70 and 72 of the connector 66 as the cap 62 is being screwed onto the connector 66, the protruding members 94 and 96 flex outwardly and slide along the outer surface of protruding members 70 and 72 until protruding members 70 and 72 are passed. Outward flex of the protruding members 94 and 96 is aided by the cut out tabs 78 and 92, which are flexed outwardly by bridges 98 and 100. Once the protruding members 94 and 96 pass protruding members 70 and 72, protruding members 94 and 96 snap inwardly configuring the child-resistant cap in the locked position. To configure the child-resistant cap 62 in the unlocked position, pressure is applied to the pressure points on tabs 78 and 92, which causes protruding members 94 and 96 to flex inwardly. Simultaneous to the application of pressure, the child-resistant cap 62 can be rotated in the counterclockwise direction to unscrew the cap 62 from the connector 66. Since protruding members 94 and 96 are flexed inwardly, they can slide along the inner surface of protruding members 70 and 72 to pass the protruding members 70 and 72.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein. The disclosures of all publications, patents, patent applications and published patent applications referred to herein are hereby incorporated herein by reference in their entirety.

EXEMPLARY EMBODIMENTS

Embodiment 1

A child-resistant topical drug applicator comprising:
a container comprising a connector and a tube configured to contain a topical pharmaceutical composition;
a sponge applicator fluidly coupled to the connector; and
a child-resistant cap that reversibly couples to the connector and encloses the sponge applicator, the cap having a locked position and an unlocked position.

Embodiment 2

The applicator of embodiment 1, wherein:
the cap comprises an inner surface having one or more protruding members; and
the connector comprises an annular rim comprising one or more notches;
wherein the cap is in the unlocked position when at least one protruding member is aligned with the notch, and the cap is in the locked position when the one or more protruding members are restrained by the rim.

Embodiment 3

The applicator of embodiment 2, wherein the rim comprises an angled or rounded edge to allow unidirectional movement of the one or more protruding members into the locked position.

Embodiment 4

The applicator of embodiment 2 or 3, wherein the connector comprises an annular grove disposed under the rim configured to receive the one or more protruding members when the cap is in the locked position.

Embodiment 5

The applicator of any one of embodiments 2-4, wherein the inner surface of the cap comprises two protruding members.

Embodiment 6

The applicator of any one of embodiments 2-4, wherein the inner surface of the cap comprises three protruding members.

Embodiment 7

The applicator of embodiment 5 or 6, wherein the protruding members are approximately evenly spaced apart.

Embodiment 8

The applicator of any one of embodiments 5-7, wherein release of at least one of the protruding members through the notch allows for the release of the remaining protruding members.

Embodiment 9

The applicator of embodiment 2, wherein the cap has a second locked position that limits rotational movement of the cap.

Embodiment 10

The applicator of embodiment 9, wherein the connector comprises a second notch that does not fully pass through the rim, wherein the first notch and the second notch are connected by a lateral groove.

Embodiment 11

The applicator of embodiment 10, wherein the second notch partially passes through the rim.

Embodiment 12

The applicator of any one of embodiments 1-11, comprising a first indicator on the cap and a second indicator on the container, wherein the first indicator and the second indicator align when the cap is in the unlocked position.

Embodiment 13

The applicator of embodiment 12, wherein the first indicator aligns with one of the one or more protruding members, and the second indicator aligns with the notch in the annular rim.

Embodiment 14

The applicator of embodiments 12 or 13, wherein the first indicator or the second indicator is a directional indicator that indicates a direction to apply a force to remove the cap.

Embodiment 15

The applicator of embodiment 1, wherein the child-resistant cap comprises one or more pressure points, wherein application of pressure to the pressure points configures the child-resistant cap in an unlocked position.

Embodiment 16

The applicator of embodiment 15, wherein the one or more pressure points are disposed on one or more cut out tabs on the child-resistant cap.

Embodiment 17

The applicator of any one of embodiments 1, 15, and 16 wherein the child-resistant cap couples to the connector through a threaded interface.

Embodiment 18

The applicator of any one of embodiments 1 and 15-17, wherein the child-resistant cap comprises an inner cap segment nested within an outer cap segment, and wherein the inner cap segment encloses the sponge applicator.

Embodiment 19

The applicator of embodiment 18, wherein the inner cap segment couples to the connector through a threaded interface, and wherein the outer cap segment comprises one or more pressure points, wherein application of pressure to the pressure points configures the child-resistant cap in an unlocked position.

Embodiment 20

The applicator of any one of embodiments 1 and 15-19, wherein the connector comprises two or more protruding members, wherein the child-resistant cap comprises two or more protruding members, and wherein the protruding members of the connector block the protruding members of the child-resistant cap when the child-resistant cap is in the locked position to limit rotational movement of the cap.

Embodiment 21

The applicator of embodiment 20, wherein the protruding members of the connector are angled or ratcheted.

Embodiment 22

The applicator of any one of embodiments 1-21, wherein the connector is integrated with the tube.

Embodiment 23

The applicator of any one of embodiments 1-22, wherein the connector and the tube are separate pieces.

Embodiment 24

The applicator of embodiment 23, wherein the connector is permanently attached to the tube.

Embodiment 25

The applicator of embodiment 23 or 24, wherein the connector is fluidly coupled to the tube through a threaded interface.

Embodiment 26

The applicator of any one of embodiments 1-25, wherein the connector and the tube comprise different materials.

Embodiment 27

The applicator of any one of embodiments 1-26, wherein the connector comprises a first material and the connector comprises a second material, and wherein the second material is harder than the first material.

Embodiment 28

The applicator of any one of embodiments 1-27, wherein the sponge applicator is permanently attached to the connector.

Embodiment 29

The applicator of any one of embodiments 1-28, further comprising a hole that traverses the sponge applicator and fluidly connects to the tube.

Embodiment 30

The applicator of embodiment 29, wherein the cap comprises a plug that fits into the hole that traverses the sponge applicator.

Embodiment 31

The applicator of embodiment 30, wherein the plug extends at least a portion of the way through the hole.

Embodiment 32

The applicator of embodiment 30 or 32, wherein the plug extends into the connector.

Embodiment 33

The applicator of any one of embodiments 30-32, wherein the plug extends into the tube.

Embodiment 34

The applicator of any one of embodiments 1-33, wherein the cap comprises a grooved or textured outer surface.

Embodiment 35

The applicator of any one of claims, 1-34, wherein the connector is attached to the distal end of the tube, and wherein the proximal end of the tube is sealed.

Embodiment 36

The applicator of any one of embodiments 1-35, further comprising a tamper-evident band.

Embodiment 37

The applicator of any one of embodiments 1-36, wherein the tube contains the topical pharmaceutical composition.

Embodiment 38

The applicator of any one of embodiments 1-37, wherein the pharmaceutical composition is a topical analgesic.

Embodiment 39

The applicator of any one of embodiments 1-38, wherein the pharmaceutical composition comprises lidocaine.

Embodiment 40

The applicator of any one of embodiments 1-39, wherein the pharmaceutical composition comprises about 2% to less than 5% lidocaine by weight.

Embodiment 41

The applicator of any one of embodiments 1-40, wherein the pharmaceutical composition comprises about 4% lidocaine by weight.

Embodiment 42

The applicator of any one of embodiments 1-41, wherein the pharmaceutical composition comprises about 5% lidocaine by weight or more.

Embodiment 43

The applicator of any one of embodiments 1-42, wherein the pharmaceutical Embodiment composition is a gel, a lotion, an ointment, a cream, or a paste.

Embodiment 44

The applicator of any one of embodiments 1-43, wherein the pharmaceutical composition comprises emu oil.

Embodiment 45

A kit comprising the applicator of any one of embodiments 1-44 and instructions for use.

Embodiment 46

A method of opening the applicator of any one of embodiments 1-45, comprising positioning in the cap in the unlocked configuration, and separating the cap from the container.

Embodiment 47

A method of applying a topical pharmaceutical composition to a surface to be treated, comprising:
separating a child-resistant cap from a container fluidly coupled to a sponge applicator, the container comprising a connector and a tube containing a topical pharmaceutical composition; and
applying the pharmaceutical composition on the sponge applicator to the surface.

Embodiment 48

The method of embodiment 47, further comprising dispensing the topical pharmaceutical composition disposed onto the sponge applicator.

Embodiment 49

The method of embodiment 47, wherein the topical pharmaceutical composition is wicked up by the sponge applicator.

Embodiment 50

The method of embodiment 48 or 49, wherein applying the pharmaceutical composition to the surface to be treated comprises rubbing or blotting the sponge applicator on the surface.

Embodiment 51

The method of any one of embodiments 47-50, further comprising positioning the cap to an unlocked position prior to separating the cap from the container.

Embodiment 52

The method of any one of embodiments 47-51, wherein the child-resistant cap is separated from the container by pulling the child-resistant cap at an angle.

Embodiment 53

The method of any one of embodiments 47-52, wherein the child-resistant cap is separated from the container by unscrewing the cap configured in an unlocked position.

Embodiment 54

The method of embodiment 53, wherein the child-resistant cap is configured in an unlocked position by applying pressure to one or more pressure points on the child-resistant cap.

Embodiment 55

The method of any one of embodiments 47-54, wherein the pharmaceutical composition is dispensed onto the sponge applicator by applying lateral pressure to the tube.

Embodiment 56

The method of any one of embodiments 47-55, wherein the pharmaceutical composition is a topical analgesic.

Embodiment 57

The method of any one of embodiments 47-56, wherein the pharmaceutical composition comprises lidocaine.

Embodiment 58

The method of any one of embodiments 47-57, wherein the pharmaceutical composition comprises about 2% to less than 5% lidocaine by weight.

Embodiment 59

The method of any one of embodiments 47-58, wherein the pharmaceutical composition comprises about 4% lidocaine by weight.

Embodiment 60

The applicator of any one of embodiments 47-59, wherein the pharmaceutical composition comprises about 5% lidocaine by weight or more.

Embodiment 61

The method of any one of embodiments 47-60, wherein the pharmaceutical composition is a gel, a lotion, an ointment, a cream, or a paste.

Embodiment 62

The method of any one of embodiments 47-61, wherein the pharmaceutical composition comprises emu oil.

Embodiment 63

A child-resistant topical drug applicator for the topical application of lidocaine, comprising:
a container comprising a connector and a tube containing a topical pharmaceutical composition comprising lidocaine;
a sponge applicator fluidly coupled to the connector; and
a child-resistant cap that reversibly couples to the connector and encloses the sponge applicator, the cap having a locked position and an unlocked position;
wherein:
the cap comprises an inner surface having three protruding members and a first indicator that indicates the position of one of the protruding members; and
the connector comprises an annular rim comprising one or more notches and a second indicator that indicates the position of the notch;
the cap is in the unlocked position when one of the protruding members is aligned with the notch, and the cap is in the locked position when none of the protruding members are aligned with the notch; and
the first indicator and the second indicator align when the cap is in the unlocked position.

Embodiment 64

A child-resistant topical drug applicator for the topical application of lidocaine, comprising:
a container comprising a connector and a tube containing a topical pharmaceutical composition comprising lidocaine;
a sponge applicator fluidly coupled to the connector; and
a child-resistant cap that reversibly couples to the connector and encloses the sponge applicator, the cap having a locked position and an unlocked position;
wherein:
the child-resistant cap comprises one or more pressure points disposed on one or more cut out tabs on the child-resistant cap, wherein application of pressure to the pressure points configures the child-resistant cap in an unlocked position;
the child-resistant cap comprises an inner cap segment nested within an outer cap segment;
the inner cap segment couples to the connector through a threaded interface and encloses the sponge applicator;
the connector comprises two or more angled or ratcheted protruding members;
the child-resistant cap comprises two or more protruding members; and
the protruding members of the connector block the protruding members of the child-resistant cap when the child-resistant cap is in the locked position to limit rotational movement of the cap.

Embodiment 65

The applicator of embodiment 63 or 64, wherein the sponge applicator comprises a hole that traverses the sponge applicator and fluidly connects the tube, and wherein the child-resistant cap comprises a plug that fits into the hole that traverses the sponge applicator.

EXAMPLE

The child-resistant topical drug applicator shown in FIG. 1 and FIGS. 2A-2C was tested among children and senior adults for ease of opening the child-resistant cap. Ease of closing the child-resistant cap was also tested in senior adults. The tube included the following instructions: (1) Rotate and Align Arrows and Base. (2) Slightly Angle Lid and Pull to Release. (3) Replace Lid, Rotate Arrows Away to Lock. Testing was conducted according to the guidelines set forth by the United States Consumer Product Safety Commission (U.S. C.P.S.C.), as published in the United States Federal Register on Jul. 21, 1995 (16 C.F.R. §§ 1700.15, 1700.20) by an independent marketing research firm specializing in the field of testing child-resistant packages.

Fifty children (25 males and 25 females) aged 42-51 months at five different testing sites attempted to open the child-resistant topical drug applicator before or after an opening demonstration. None of the children successfully opened the package prior to demonstration during 10 minutes of testing. One child was able to open the package following demonstration during 10 minutes of testing. These results show 100% child-resistant effectiveness before demonstration and 98% child-resistant effectiveness after demonstration.

Separately, 100 senior adults (30 males and 70 females) aged 50-70 years at fifteen different testing sites attempted to open (two identical devices) or close (one device) the child-resistant topical drug applicator. One senior adult failed to open the first device, and no senior adults failed to open the second device. None of the senior adults failed to close the second package. The results show a senior adult use effectiveness of 99%.

What is claimed is:
1. A child-resistant topical drug applicator comprising:
a container comprising a connector and a tube containing a topical pharmaceutical composition, wherein the connector comprises an annular rim comprising one or more notches;
a sponge applicator fluidly coupled to the connector; and
a child-resistant cap that reversibly couples to the connector and encloses the sponge applicator, the cap comprising an inner surface having one or more protruding members, wherein the cap is in an unlocked position when at least one protruding member is aligned with at least one of the one or more notches, and the cap is in a locked position when the one or more protruding members are restrained by the annular rim;
wherein the cap and the connector are configured so that the cap can transition from the locked position to the unlocked position without applying a downward force to the cap.

2. The applicator of claim 1, wherein the rim comprises an angled or rounded edge to allow unidirectional movement of the one or more protruding members into the locked position.

3. The applicator of claim 1, wherein the connector comprises an annular groove disposed under the rim configured to receive the one or more protruding members when the cap is in the locked position.

4. The applicator of claim 1, wherein the inner surface of the cap comprises two or more protruding members.

5. The applicator of claim 4, wherein release of at least one of the protruding members through one of the one or more notches allows for the release of the remaining protruding members.

6. The applicator of claim 1, comprising a first indicator on the child-resistant cap and a second indicator on the container, wherein the first indicator and the second indicator align when the cap is in the unlocked position.

7. The applicator of claim 6, wherein the first indicator aligns with one of the one or more protruding members, and the second indicator aligns with one of the one or more notches in the annular rim.

8. The applicator of claim 6, wherein the first indicator or the second indicator is a directional indicator that indicates a direction to apply a force to remove the child-resistant cap.

9. The applicator of claim 1, wherein the connector comprises two or more protruding members, wherein the child-resistant cap comprises two or more protruding members, and wherein the protruding members of the connector block the protruding members of the child-resistant cap when the child-resistant cap is in the locked position to limit rotational movement of the cap.

10. The applicator of claim 9, wherein the protruding members of the connector are angled or ratcheted.

11. The applicator of claim 1, further comprising a hole that traverses the sponge applicator and fluidly connects to the tube.

12. The applicator of claim 11, wherein the child-resistant cap comprises a plug that fits into the hole that traverses the sponge applicator.

13. The applicator of claim 1, further comprising a tamper-evident band.

14. The applicator of claim 1, wherein the pharmaceutical composition is a topical analgesic.

15. The applicator of claim 1, wherein the pharmaceutical composition comprises lidocaine.

16. The applicator of claim 1, wherein the pharmaceutical composition comprises emu oil.

17. A method of opening the applicator of claim 1, comprising positioning in the cap in the unlocked configuration, and separating the cap from the container.

18. A method of applying a topical pharmaceutical composition to a surface to be treated, comprising:
    separating a child-resistant cap from a container fluidly coupled to a sponge applicator, the container comprising a connector and a tube containing a topical pharmaceutical composition, wherein the connector comprises an annular rim comprising one or more notches, the cap is configured to enclose the sponge applicator, the cap comprises an inner surface having one or more protruding members, the cap is in an unlocked position when at least one protruding member is aligned with at least one of the one or more notches, and the cap is in a locked position when the one or more protruding members are restrained by the annular rim, and separating the cap from the container comprises positioning the cap to an unlocked position from a locked position without applying a downward force to the cap; and
    applying the pharmaceutical composition on the sponge applicator to the surface.

19. The method of claim 18, wherein the child-resistant cap is separated from the container by pulling the child-resistant cap at an angle.

20. A child-resistant topical drug applicator for the topical application of lidocaine, comprising:
    a container comprising a connector and a tube containing a topical pharmaceutical composition comprising lidocaine;
    a sponge applicator fluidly coupled to the connector; and
    a child-resistant cap that reversibly couples to the connector and encloses the sponge applicator, the cap having a locked position and an unlocked position;
    wherein:
        the cap comprises an inner surface having three protruding members and a first indicator that indicates the position of one of the protruding members;
        the connector comprises an annular rim comprising one or more notches and a second indicator that indicates the position of the notch;
        the cap is in the unlocked position when one of the protruding members is aligned with the notch, the cap is in the locked position when none of the protruding members are aligned with the notch, and the cap and the connector are configured so that the cap can transition from the locked position to the unlocked position without applying a downward force to the cap; and
        the first indicator and the second indicator align when the cap is in the unlocked position.

21. The applicator of claim 20, wherein the sponge applicator comprises a hole that traverses the sponge applicator and fluidly connects the tube, and wherein the child-resistant cap comprises a plug that fits into the hole that traverses the sponge applicator.

22. A child-resistant topical drug applicator for the topical application of lidocaine, comprising:
    a container comprising a connector and a tube containing a topical pharmaceutical composition comprising lidocaine;
    a sponge applicator fluidly coupled to the connector; and
    a child-resistant cap that reversibly couples to the connector and encloses the sponge applicator, the cap having a locked position and an unlocked position;
    wherein:
        the child-resistant cap comprises one or more pressure points disposed on one or more cut out tabs on the child-resistant cap, wherein application of pressure to the pressure points configures the child-resistant cap in an unlocked position;
        the child-resistant cap comprises an inner cap segment nested within an outer cap segment, and a plurality of stability bridges between the inner cap segment and the outer cap segment;
        the inner cap segment couples to the connector through a threaded interface and encloses the sponge applicator;
        the connector comprises two or more angled or ratcheted protruding members;
        the child-resistant cap comprises two or more protruding members; and
        the protruding members of the connector block the protruding members of the child-resistant cap when the child-resistant cap is in the locked position to limit rotational movement of the cap.

23. The applicator of claim 22, wherein the sponge applicator comprises a hole that traverses the sponge applicator and fluidly connects the tube, and wherein the child-resistant cap comprises a plug that fits into the hole that traverses the sponge applicator.

24. A child-resistant topical drug applicator comprising:
a container comprising a connector and a tube containing a topical pharmaceutical composition;
a sponge applicator fluidly coupled to the connector; and
a child-resistant cap that reversibly couples to the connector and encloses the sponge applicator, the cap having a locked position and an unlocked position;
wherein:
the connector comprises two or more protruding members, wherein the cap comprises two or more protruding members, and the protruding members of the connector block the protruding members of the child-resistant cap when the child-resistant cap is in the locked position to limit rotational movement of the cap;
the child-resistant cap comprises one or more pressure points, wherein application of pressure to the pressure points configures the child-resistant cap in the unlocked position; and
wherein the child-resistant cap comprises an inner cap segment nested within an outer cap segment and a plurality of stability bridges between the inner cap segment and the outer cap segment, and wherein the inner cap segment encloses the sponge applicator.

25. The applicator of claim 24, wherein the one or more pressure points are disposed on one or more cut out tabs on the child-resistant cap.

26. The applicator of any one of claim 24, wherein the child-resistant cap couples to the connector through a threaded interface.

27. The applicator of claim 24, wherein the inner cap segment couples to the connector through a threaded interface.

28. The applicator of claim 24, wherein the protruding members of the connector are angled or ratcheted.

29. The applicator of claim 24, further comprising a hole that traverses the sponge applicator and fluidly connects to the tube.

30. The applicator of claim 29, wherein the child-resistant cap comprises a plug that fits into the hole that traverses the sponge applicator.

* * * * *